(12) United States Patent
Jiang

(10) Patent No.: US 11,941,908 B2
(45) Date of Patent: Mar. 26, 2024

(54) OPTICAL FINGERPRINT MODULE AND SIGNAL PROCESSING METHOD

(71) Applicant: BEIJING XIAOMI MOBILE SOFTWARE CO., LTD., Beijing (CN)

(72) Inventor: Zhongsheng Jiang, Beijing (CN)

(73) Assignee: BEIJING XIAOMI MOBILE SOFTWARE CO., LTD., Beijing (CN)

( * ) Notice: Subject to any disclaimer, the term of this patent is extended or adjusted under 35 U.S.C. 154(b) by 201 days.

(21) Appl. No.: 17/205,342

(22) Filed: Mar. 18, 2021

(65) Prior Publication Data
US 2021/0397807 A1    Dec. 23, 2021

(30) Foreign Application Priority Data

Jun. 17, 2020 (CN) .......................... 202010556453.8

(51) Int. Cl.
| | | |
|---|---|---|
| *G06V 40/13* | (2022.01) | |
| *A61B 5/024* | (2006.01) | |
| *A61B 5/145* | (2006.01) | |
| *G06F 3/041* | (2006.01) | |
| *G06F 3/042* | (2006.01) | |

(52) U.S. Cl.
CPC .......... *G06V 40/1318* (2022.01); *A61B 5/024* (2013.01); *A61B 5/14542* (2013.01); *G06F 3/0412* (2013.01); *G06F 3/0421* (2013.01)

(58) Field of Classification Search
CPC ... A61B 5/024; A61B 5/1172; A61B 5/14542; A61B 5/6898; A61B 5/14551; A61B 5/02444; A61B 5/7225; A61B 5/02416; A61B 5/02438; G06V 40/1318; G06F 3/0421; G06F 3/0412
See application file for complete search history.

(56) References Cited

U.S. PATENT DOCUMENTS

2017/0220844 A1    8/2017 Jones et al.
2018/0173343 A1*   6/2018 Pi ......................... A61B 5/1172

FOREIGN PATENT DOCUMENTS

CN      107580709 A      1/2018

OTHER PUBLICATIONS

European Patent Application No. 21165093.2 extended Search Report and Opinion, dated Feb. 7, 2022, 16 pages.
European Patent Application No. 21165093.2 Search Report and Opinion, dated Sep. 28, 2021, 18 pages.
Chinese Patent Application No. 202010556453.8, Office Action dated Nov. 16, 2023, 7 pages.
Chinese Patent Application No. 202010556453.8, English translation of Office Action dated Nov. 16, 2023, 7 pages.

* cited by examiner

*Primary Examiner* — Yaron Cohen
(74) *Attorney, Agent, or Firm* — COZEN O'CONNOR

(57) ABSTRACT

An optical fingerprint module and a method for processing a signal includes a light sensing unit, a signal processing unit and a control unit. The light sensing unit is configured to collect a light signal. The signal processing unit is connected to the light sensing unit and is configured to process the light signal collected by the light sensing unit to generate at least one of a fingerprint signal and a health signal. The control unit is connected to the signal processing unit and is configured to generate fingerprint information for fingerprint recognition based on the fingerprint signal output by the signal processing unit, and generate health parameter information based on a health signal output by the signal processing unit.

16 Claims, 11 Drawing Sheets

OPTICAL FINGERPRINT MODULE AND SIGNAL PROCESSING METHOD

CROSS REFERENCE TO RELATED APPLICATIONS

This application claims priority and benefits to Chinese Application No. 202010556453.8, filed on Jun. 17, 2020, the entire content of which is incorporated herein by reference.

TECHNICAL FIELD

The present disclosure relates to the field of communication, in particular to an optical fingerprint module and a method for processing a signal.

BACKGROUND

With the continuous improvement of material life, people are more and more concerned about their own health. In order to facilitate users to know their own health conditions, many electronic devices are equipped with health sensors to allow the users to better monitor their own health conditions.

SUMMARY

Embodiments of the present disclosure provide an optical fingerprint module. The optical fingerprint module includes a light sensing unit, a signal processing unit and a control unit. The light sensing unit is configured to collect a light signal. The signal processing unit is connected to the light sensing unit and is configured to generate at least one of a fingerprint signal and a health signal by processing the light signal collected by the light sensing unit. The control unit is connected to the signal processing unit and is configured to generate fingerprint information for fingerprint recognition based on the fingerprint signal output by the signal processing unit and generate health parameter information based on the health signal output by the signal processing unit.

Embodiments of the present disclosure provide an electronic device. The electronic device includes a touch and display module and an optical fingerprint module. An assembly position of the optical fingerprint module corresponds to a fingerprint recognition region formed on the touch and display module. The optical fingerprint module includes a light sensing unit, a signal processing unit and a control unit. The light sensing unit is configured to collect a light signal. The signal processing unit is connected to the light sensing unit and is configured to generate at least one of a fingerprint signal and a health signal by processing the light signal collected by the light sensing unit. The control unit is connected to the signal processing unit and is configured to generate fingerprint information for fingerprint recognition based on the fingerprint signal output by the signal processing unit and generate health parameter information based on the health signal output by the signal processing unit.

Embodiments of the present disclosure provide a method for processing a signal. The method is applied to an electronic device. The electronic device includes an optical fingerprint module. The method includes determining a pre-defined health testing condition and a pre-defined fingerprint recognition condition; inputting a first light signal for health testing collected by a light sensing unit to a signal processing unit of the optical fingerprint module, and generating health parameter information based on a health signal output by the signal processing unit, in cases that the health testing condition is met; and inputting a second light signal for fingerprint recognition collected by the light sensing unit to the signal processing unit of the optical fingerprint module and generating fingerprint information for the fingerprint recognition based on a fingerprint signal output by the signal processing unit in cases that the fingerprint recognition condition is met.

BRIEF DESCRIPTION OF THE DRAWINGS

The drawings herein are incorporated into the specification and form a part of the specification, illustrating embodiments that conform to the disclosure, and being used to explain the principle of the disclosure together with the specification.

DETAILED DESCRIPTION

Figure 1:
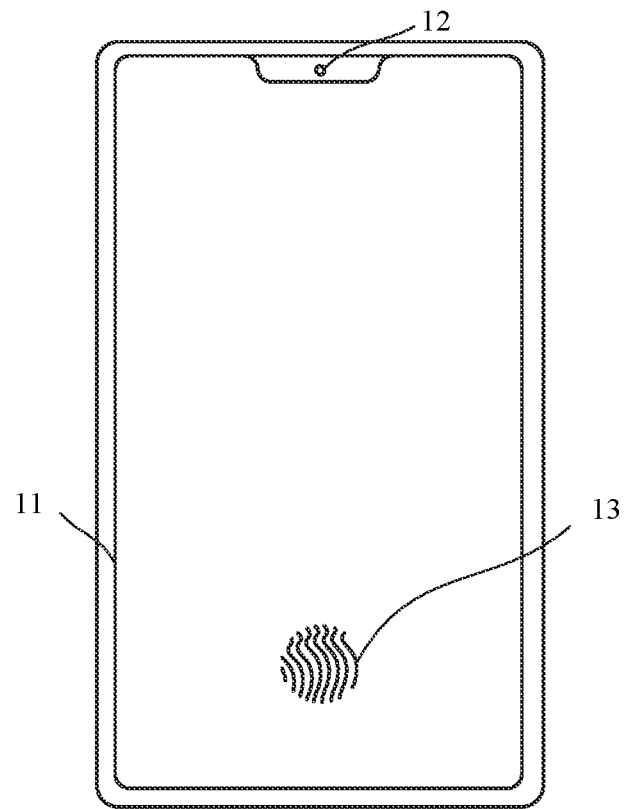
FIG. 1 is a schematic diagram illustrating a smart phone with a separately arranged health sensor according to some embodiments of the present disclosure.

The exemplary embodiments will be described in detail here, and examples thereof are shown in the accompanying drawings. When the following description refers to the accompanying drawings, unless otherwise indicated, the same numbers in different drawings represent the same or similar elements. The implementation manners described in the following exemplary embodiments do not represent all implementation manners consistent with the present disclosure. Rather, they are only examples of devices and methods consistent with some aspects of the present disclosure as detailed in the appended claims.

The terms used in the present disclosure are only used for the purpose of describing specific embodiments, and are not intended to limit the present disclosure. The singular forms "a", "an" and "the" used in the present disclosure and appended claims are also intended to include plural forms, unless the context clearly indicates other meanings. It should also be understood that the term "and/or" used herein refers to and includes any or all possible combinations of one or more associated listed items.

It should be understood that although the terms first, second, third, etc. may be used in the disclosure to describe various information, the information should not be limited to these terms. These terms are only used to distinguish the same type of information from each other. For example, without departing from the scope of the present disclosure, the first information may also be referred to as second information, and similarly, the second information may also be referred to as first information. Depending on the context, the word "if" as used herein can be interpreted as "when", "upon" or "in response to determining".

With the continuous improvement of material life, people are more and more concerned about their own health. In order to facilitate users to understand their own health conditions, many electronic devices are equipped with health sensors to allow the users to better monitor their own health conditions.

In the related art, the health sensor is separately arranged outside the touch and display module (also called a touch screen) of the electronic device. Taking the smart phone illustrated in FIG. 1 as an example, a touch and display module 11 and a health sensor 12 are installed on the front of the smart phone. A region at a top region of the smart phone is specially vacated for arranging the health sensor 12. It can be seen that the separate arrangement of the health sensor not only affects the appearance of the smart phone, but also reduces the ratio of an area of the screen to an area of the front panel of the smart phone. In addition to arranging the health sensor at the top region of the smart phone, in the related arts, the health sensor may be also arranged on the backplane of the electronic device. This arrangement requires arranging an opening on the backplane, which not only affects the industrial design of the backplane, but also reduces the mechanical strength of the backplane.

In addition to the health sensor, in order to ensure the safety of the device, in the related arts, under-screen fingerprint sensors may be regularly distributed below the touch and display module to form a fingerprint recognition region 13 as illustrated in FIG. 1 in the touch and display module.

In view of this, the present disclosure proposes an optical fingerprint module, integrating the health sensor and the fingerprint sensor into the same module, thereby avoiding the problem of occupying the layout space by arranging the health sensor.

Figure 2:
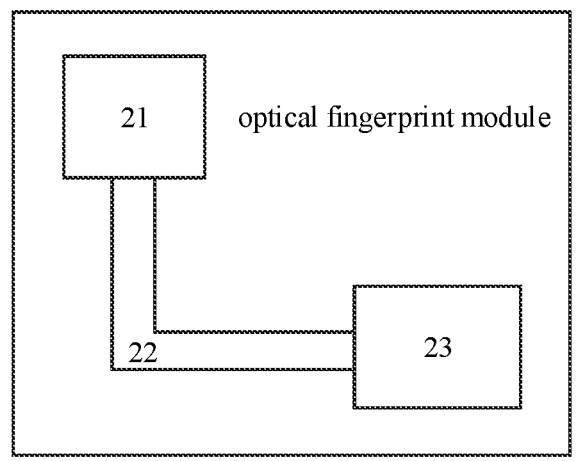
FIG. 2 is a schematic diagram illustrating an optical fingerprint module according to some embodiments of the present disclosure.

FIG. 2 is a schematic diagram illustrating an optical fingerprint module according to some embodiments of the present disclosure. As illustrated in FIG. 2, the optical fingerprint module may include a light sensing unit 21, a signal processing unit 22 and a control unit 23.

The light sensing unit 21 is configured to collect the light signal(s).

The signal processing unit 22 is connected to the light sensing unit and is configured to process the light signal(s) collected by the light sensing unit to generate the fingerprint signal(s) and/or the health signal(s).

The control unit 23 is connected to the signal processing unit and is configured to generate fingerprint information for fingerprint recognition based on the fingerprint signal(s) output by the signal processing unit and generate health parameter information based on the health signal(s) output by the signal processing unit.

In the present disclosure, both the light sensing unit 21 and the signal processing unit 22 may have various structures, as long as the operation of collecting the light signals and processing the light signals can be realized, which are not limited in the present disclosure.

Figure 3:
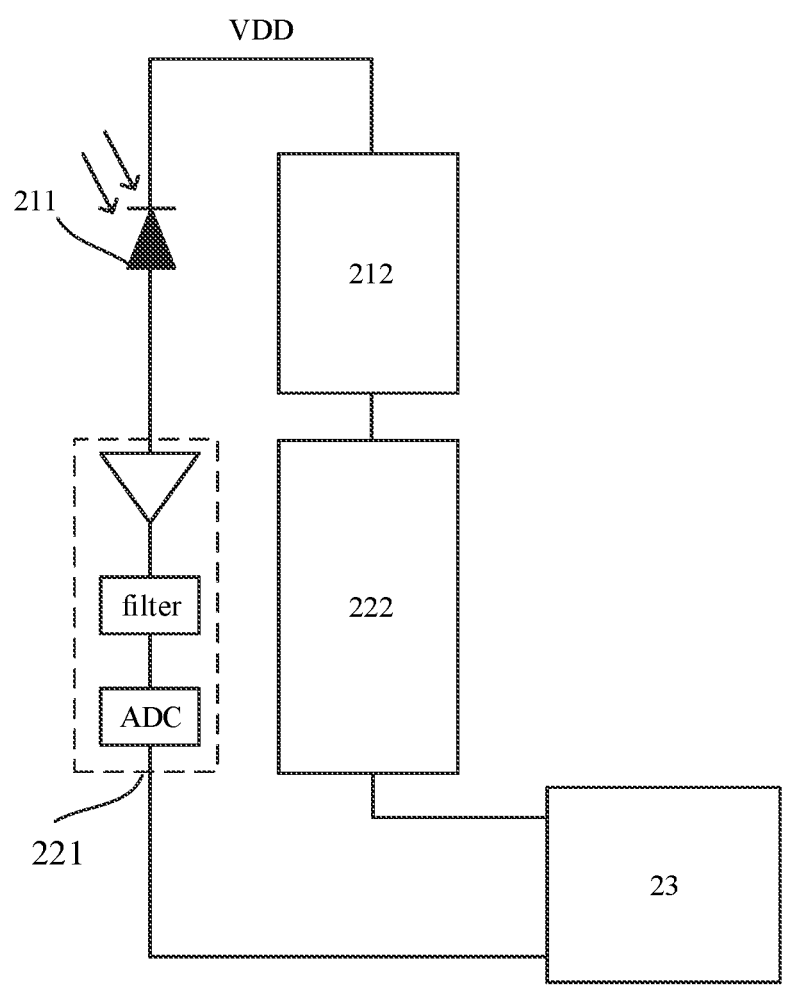
FIG. 3 is a first logical schematic diagram of an optical fingerprint module according to some embodiments of the present disclosure.

In some embodiments, the light sensing unit 21 may include a fingerprint sensor 211 and a health sensor 212 as illustrated in FIG. 3. The signal processing unit 22 may include a fingerprint signal processing circuitry 221 and a health signal processing circuitry 222. The fingerprint sensor 211 is configured to collect light signals for the fingerprint recognition. The health sensor 212 is configured to collect light signals for health testing. The fingerprint signal processing circuitry 221 is connected to the fingerprint sensor 211 and is configured to process the light signals collected by the fingerprint sensor 211 to obtain the fingerprint signal. The health signal processing circuitry 222 is configured to process the light signals collected by the health sensor 212 to obtain the health signal. The control unit 23 is connected to both the fingerprint signal processing circuitry 221 and the health signal processing circuitry 222 and is configured to generate the fingerprint information for the fingerprint recognition based on the fingerprint signal output by the fingerprint signal processing circuitry 221 and generate the health parameter information based on the health signal output by the health signal processing circuitry 222. In this case, the fingerprint sensor, the fingerprint signal processing circuitry 221 and the control unit 23 connected in series are used for the fingerprint recognition. The health sensor 212, the health signal processing circuitry 222 and the control unit 23 connected in series are used for the health testing. In other words, the fingerprint recognition and the health testing have respective dedicated sensors and signal processing circuitry. The fingerprint recognition and the health testing are independent of each other, thereby reducing mutual interference between the fingerprint signal and the health signal and improving the accuracy of the fingerprint recognition and the health testing.

Figure 4:
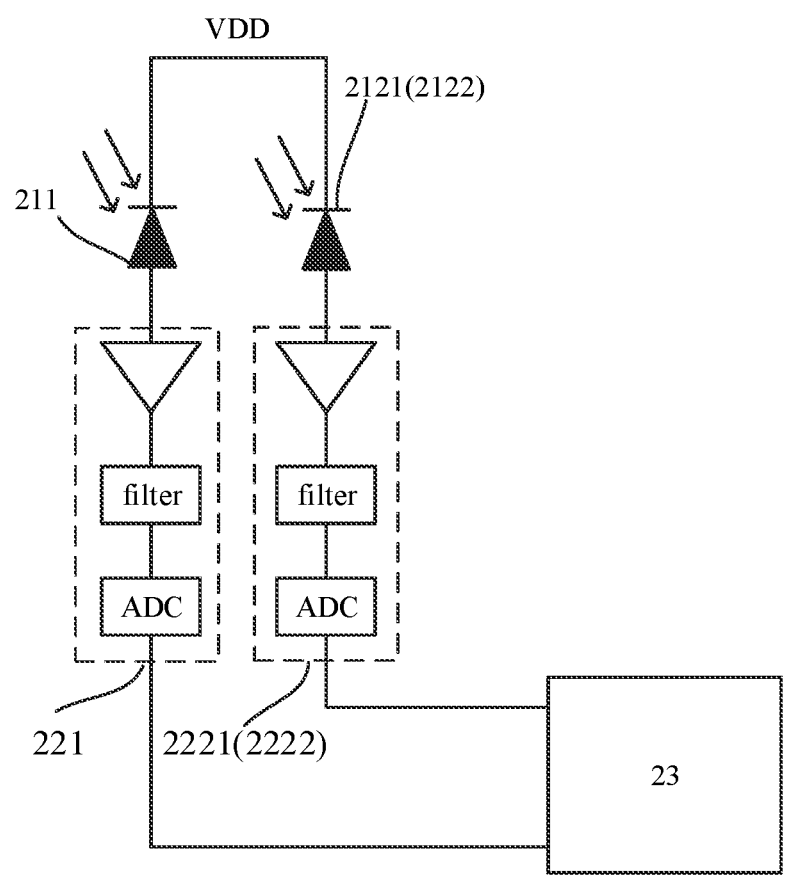
FIG. 4 is a second logical schematic diagram of an optical fingerprint module according to some embodiments of the present disclosure.
Figure 5:
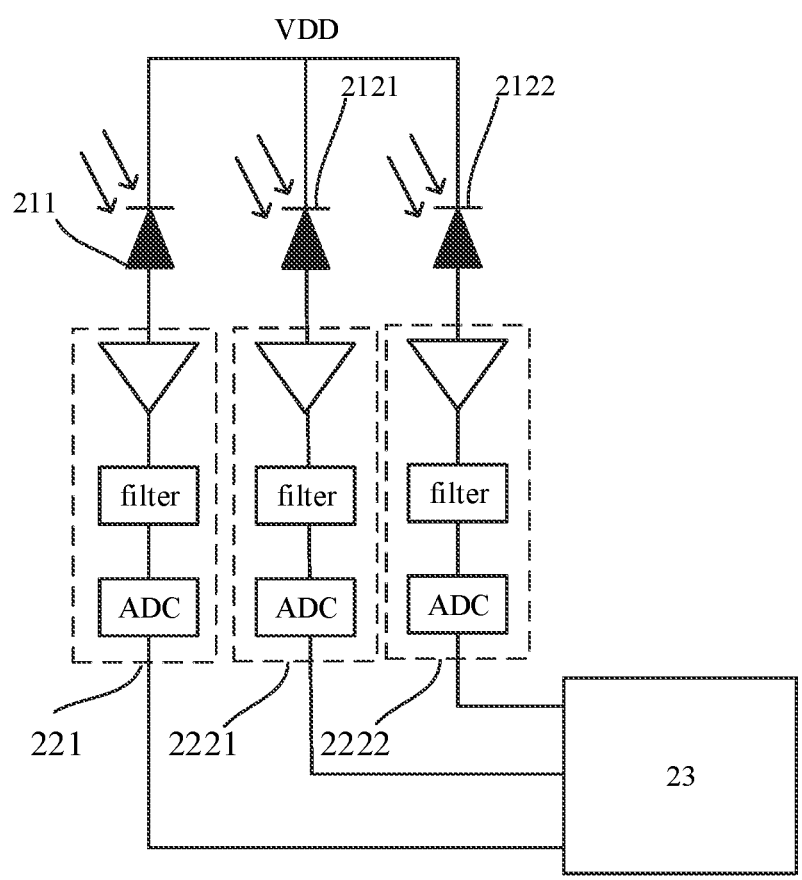
FIG. 5 is a third logical schematic diagram of an optical fingerprint module according to some embodiments of the present disclosure.

Since in practical applications, the health testing can be performed by red light or green light, the health sensor may include a red light sensor 2121 and/or a green light sensor 2122. The red light sensor 2121 is configured to collect red light for the health testing. The green light sensor 2122 is configured to collect green light for the health testing. Correspondingly, the health signal processing circuitry 222 may include a red light signal processing circuitry 2221 and/or a green light signal processing circuitry 2222. The red light signal processing circuitry 2221 is connected to the red light sensor 2121 and is configured to process the red light collected by the red light sensor 2121 to obtain the red light signal. The green light signal processing circuitry 2222 is connected to the green light sensor 2122 and is configured to process the green light collected by the green light sensor 2122 to obtain the green light signal. Correspondingly, the control unit 23 is connected to the fingerprint signal processing circuitry 221 and is configured to generate the fingerprint information for the fingerprint recognition based on the fingerprint signal output by the fingerprint signal processing circuitry 221. The control unit is also connected to the red light signal processing circuitry 2221 and/or the green light signal processing circuitry 2222 and is configured to generate the health parameter information based on the red light signal output by the red light signal processing circuitry 2221 and/or generate the health parameter information based on the green light signal output by the green light signal processing circuitry 2222. Logical diagrams are illustrated as FIGS. 4 and 5.

In some embodiments, the fingerprint sensor 211 may be reused as the red light sensor 2121 and/or the green light sensor 2122 as described above. That is, the fingerprint sensor 211 may be also functioned as the red light sensor 2121 and/or the green light sensor 2122. In some embodiments, the light sensing unit 21 may include only the fingerprint sensor 211, and the signal processing unit may include both the fingerprint signal processing circuitry 221 and the red light signal processing circuitry 2221, both the fingerprint signal processing circuitry 221 and the green light signal processing circuitry 2222, or all of the fingerprint signal processing circuitry 221, the red light signal processing circuitry 2221 and the green light signal processing circuitry 2222. Correspondingly, the optical fingerprint module may further include a first circuit gating switch 241. The logical diagrams of the above three cases are illustrated as FIGS. 6 to 8.

Figure 6:
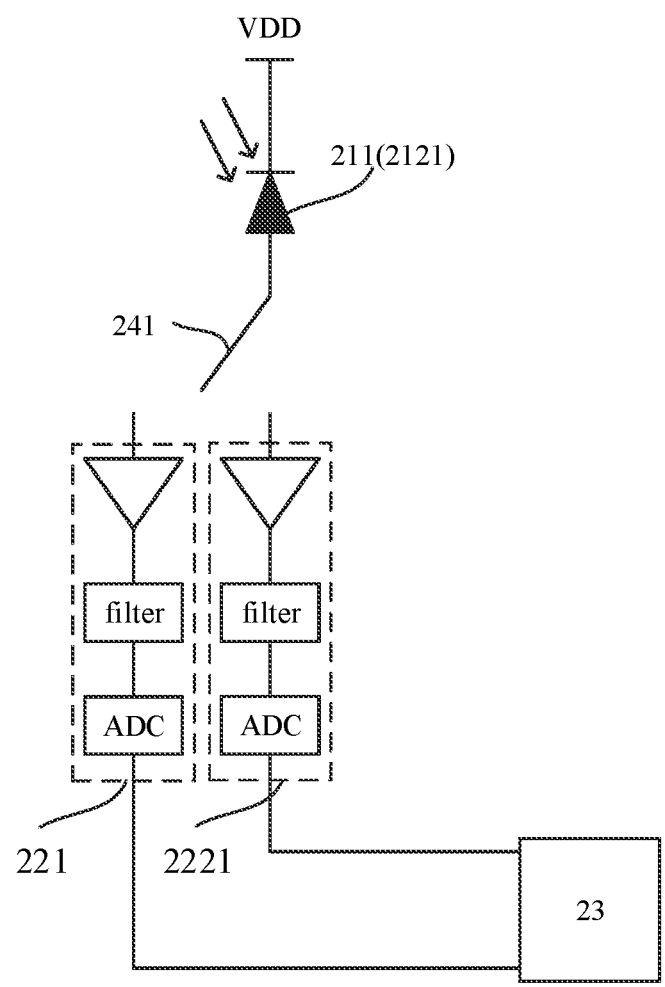
FIG. 6 is a fourth logical schematic diagram of an optical fingerprint module according to some embodiments of the present disclosure.

In some embodiments, when the logical diagram is illustrated as FIG. 6, the fingerprint sensor 211 is configured to collect light signals for the fingerprint recognition and collect red light for the health testing. The fingerprint signal processing circuitry 221 is connected to the control unit 23 and is configured to process the light signals collected by the fingerprint sensor 211 to obtain the fingerprint signal. The red light signal processing circuitry 2221 is connected to the control unit 23 and is configured to process the red light collected by the fingerprint sensor 211 to obtain the red light signal. One terminal of the first circuit gating switch 241 is connected to the fingerprint sensor 211, and the other terminal is connected to either the fingerprint signal processing circuitry 221 or the red light signal processing circuitry 2221. The control unit 23 is configured to generate the fingerprint information for the fingerprint recognition based on the fingerprint signal output from the fingerprint signal processing circuitry 221 and generate the health parameter information generated based on the red light signal output by the red light signal processing circuitry 2221.

Figure 7:
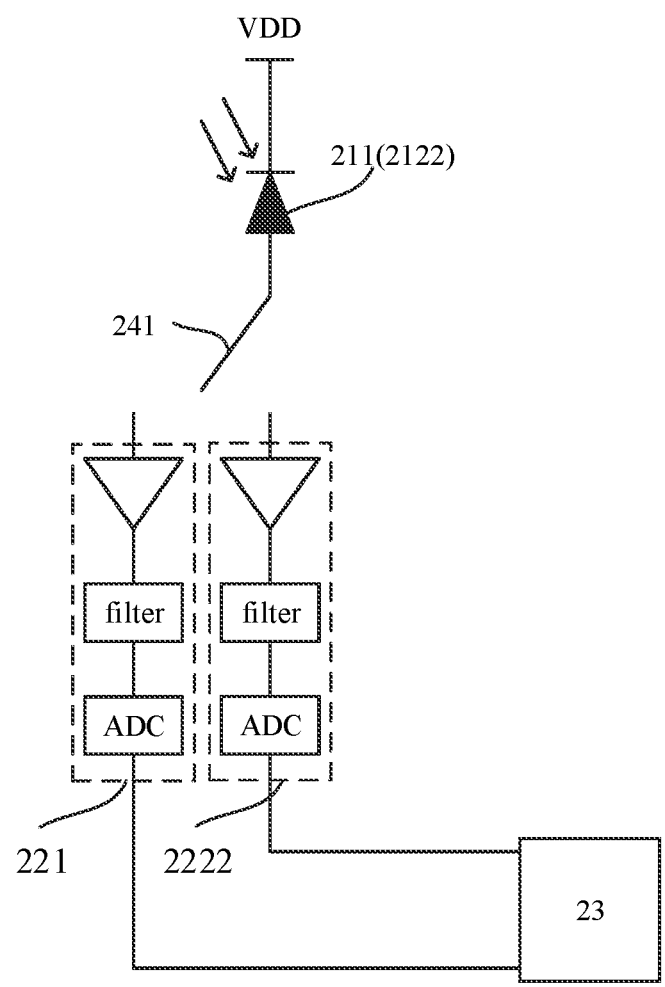
FIG. 7 is a fifth logical schematic diagram of an optical fingerprint module according to some embodiments of the present disclosure.

In some embodiments, when the logical diagram is illustrated as FIG. 7, the fingerprint sensor 211 is configured to collect light signals for the fingerprint recognition and collect green light for the health testing. The fingerprint signal processing circuitry 221 is connected to the control unit 23 and is configured to process the light signals collected by the fingerprint sensor 211 to obtain the fingerprint signal. The green light signal processing circuitry 2222 is connected to the control unit 23 and is configured to process the green light collected by the fingerprint sensor 211 to obtain the green light signal. One terminal of the first circuit gating switch 241 is connected to the fingerprint sensor 211, and the other terminal is connected to either the fingerprint signal processing circuitry 221 or the green light signal processing circuitry 2222. The control unit 23 is configured to generate the fingerprint information for the fingerprint recognition based on the fingerprint signal output from the fingerprint signal processing circuitry 221 and generate the health parameter information based on the green light signal output by the green light signal processing circuitry 2222.

Figure 8:
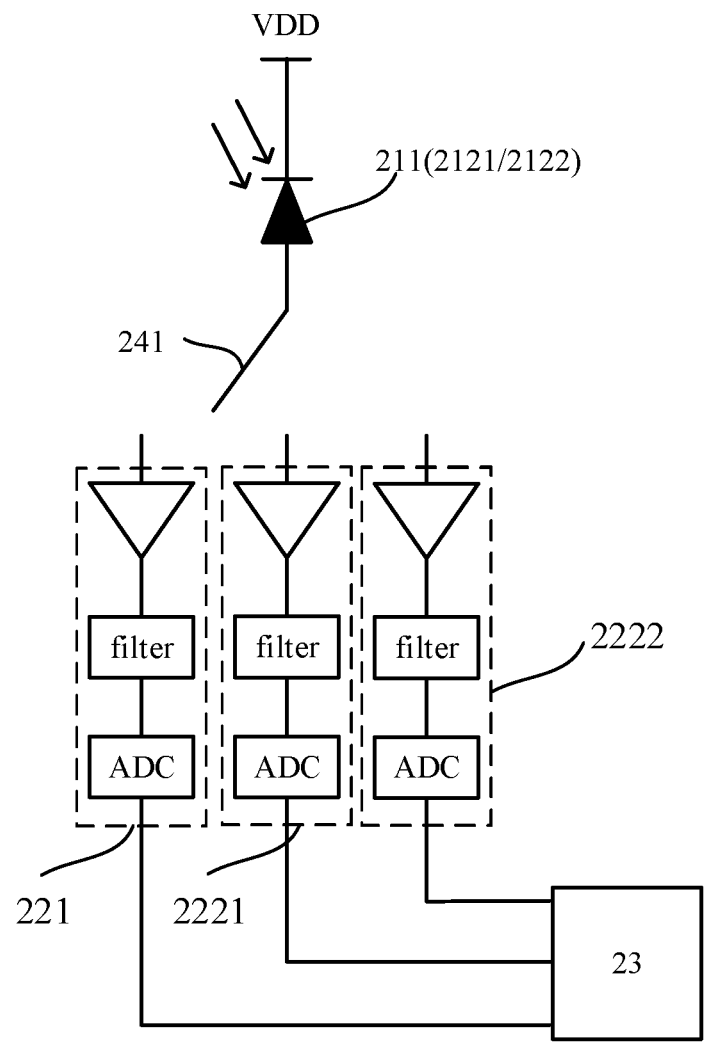
FIG. 8 is a sixth logical schematic diagram of an optical fingerprint module according to some embodiments of the present disclosure.

In some embodiments, when the logical diagram is illustrated as FIG. 8, the fingerprint sensor 211 is configured to collect light signals for the fingerprint recognition, the red light and the green light for the health testing. The fingerprint signal processing circuitry 221 is connected to the control unit 23 and is configured to process the light signals collected by the fingerprint sensor 211 to obtain the fingerprint signal. The red light signal processing circuitry 2221 is connected to the control unit 23 and is configured to process the red light collected by the fingerprint sensor 211 to obtain the red light signal. The green light signal processing circuitry 2222 is connected to the control unit 23 and is configured to process the green light collected by the fingerprint sensor 211 to obtain the green light signal. One terminal of the first circuit gating switch 241 is connected to the fingerprint sensor 211, and the other terminal is connected to one of the fingerprint signal processing circuitry 221, the red light signal processing circuitry 2221 and the green light signal processing circuitry 2222. The control unit 23 is configured to generate fingerprint information for the fingerprint recognition based on the fingerprint signal output by the fingerprint signal processing circuitry 221, generate the health parameter information based on the red light signal output by the red light signal processing circuitry 2221, and generate the health parameter information based on the green light signal output by the green light signal processing circuitry 2222.

In some embodiments, the fingerprint sensor is reused as (or also functioned as) a red light sensor and/or a green light sensor. Therefore, there is no need to additionally arrange a health sensor in the electronic device having the optical fingerprint module, thereby solving a problem that the ratio of the area of the screen to the area of the front panel of the electronic device is reduced by separately arranging the health sensor, reducing the number of sensors to be deployed, and reducing hardware costs.

Figure 9:
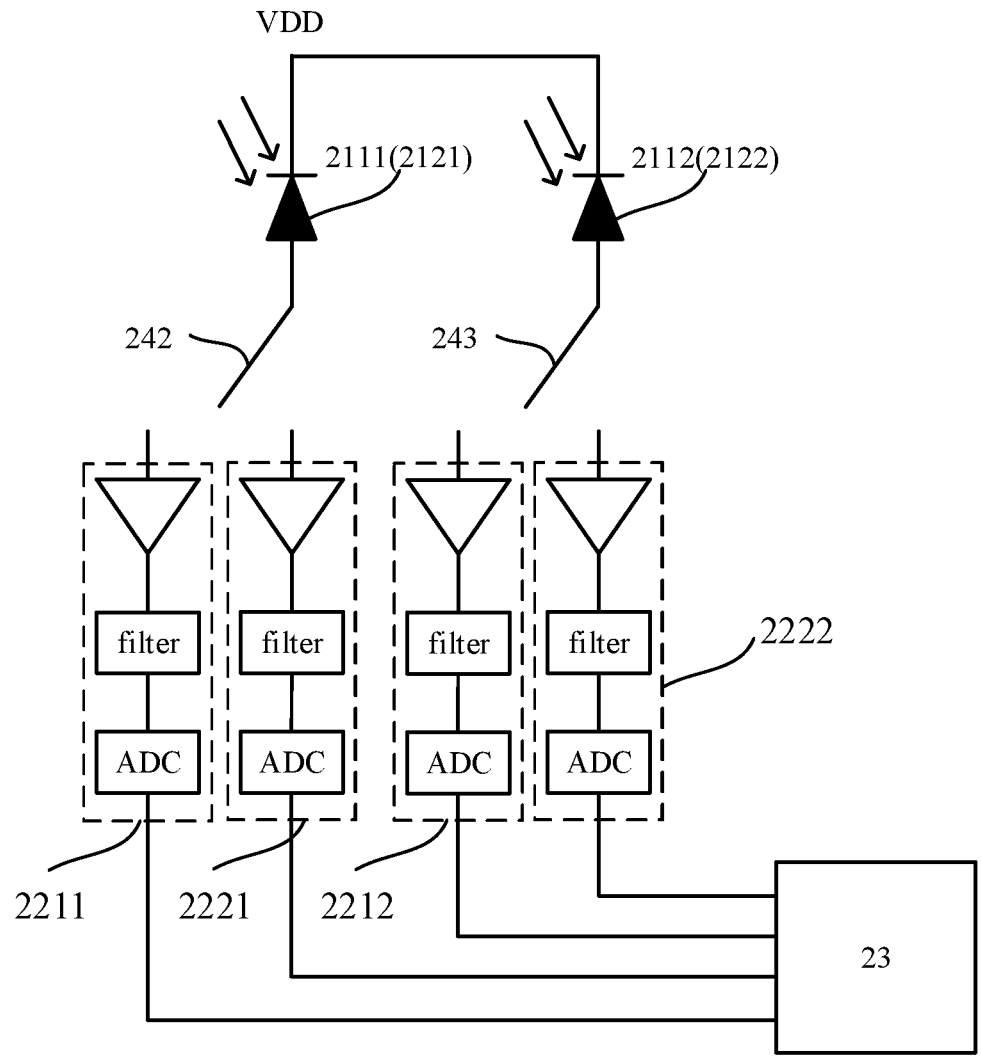
FIG. 9 is a seventh logical schematic diagram of an optical fingerprint module according to some embodiments of the present disclosure.

In some embodiments, two fingerprint sensors can be reused respectively as the red light sensor 2121 and the green light sensor 2122. In this case, the light sensing unit 21 may include a first fingerprint sensor 2111 and a second fingerprint sensor 2112. The signal processing unit 22 may include a first fingerprint signal processing circuitry 2211, a red light signal processing circuitry 2221, a second fingerprint signal processing circuitry 2212 and a green light signal processing circuitry 2222. Correspondingly, a second circuit gating switch 242 and a third circuit gating switch 243 may be also included. Details are illustrated in FIG. 9. The first fingerprint sensor 2111 is configured to collect light signals for the fingerprint recognition and the red light for the health testing. The second fingerprint sensor 2112 is configured to collect light signals for the fingerprint recognition and the green light for the health testing. The first fingerprint signal processing circuitry 2211 is connected to the control unit 23 and is configured to process the light signals collected by the first fingerprint sensor 2111 to obtain the first fingerprint signal. The red light signal processing circuitry 2221 is connected to the control unit 23 and is configured to process the red light collected by the first fingerprint sensor 2111 to obtain the red light signal. The second fingerprint signal processing circuitry 2212 is connected to the control unit 23 and is configured to process the light signals collected by the second fingerprint sensor 2112 to obtain the second fingerprint signal. The green light signal processing circuitry 2222 is connected to the control unit 23 and is configured to process the green light collected by the second fingerprint sensor 2112 to obtain the green light signal. One terminal (or end) of the second circuit gating switch 242 is connected to the first fingerprint sensor 2111, and the other end is connected to either the first fingerprint signal processing circuitry 2211 or the red light signal processing circuitry 2221. One terminal of the third circuit gating switch 243 is connected to the second fingerprint sensor 2112, and the other terminal is connected to either the second fingerprint signal processing circuitry 2212 or the green light signal processing circuitry 2222. The control unit 23 is configured to generate fingerprint information for the fingerprint recognition based on the first fingerprint signal output by the first fingerprint signal processing circuitry 2211 and/or the second fingerprint signal output by the second fingerprint signal processing circuitry 2212, generate the health parameter information based on the red light signal output by the red light signal processing circuitry 2221, and generate the health parameter information based on the green light signal output by the green light signal processing circuitry 2222. In some embodiments, two different sensors are reused respectively as the red light sensor and the green light sensor. Compared with the embodiments as mentioned above, one fingerprint sensor in embodiments of FIG. 9 is reused as a sensor for processing a light signal of a single color, thereby reducing the color types of light signals to be collected by a single sensor and accordingly reducing the burden of the fingerprint sensor.

In the above embodiments of collecting the red light signals and the green light signals, the red light signal and the green light signal may be separately obtained for the health testing, and the red light signal or the green light signal which has a higher stability can be further used as the health signal to generate the health parameter information. It can be understood that, the red light and the green light may be interfered differently in different environments, which will affect the results of the health testing. It can be seen that with the method, selection may be performed on the red light signal and the green light signal to determine the a signal that is less interfered for the health testing, thereby improving the accuracy of the health testing.

The health testing may be made usually by sending a beam of light to the human body and evaluating the health of the human body based on changes in the returned beam of light. Therefore, the optical fingerprint module may also include a health signal emitting end. For example, the optical fingerprint module may include a red light emitting end and/or a green light emitting end. The red light emitting end is configured to emit the red light for the health testing, and the green light emitting end is configured to emit the green light for the health testing.

The light signals collected by the present disclosure for the health testing may be monochromatic light, such as the red light and the green light as described above, and the health sensor may be a red light sensor or a green light sensor accordingly. In addition to monochromatic light, the light signals can also be infrared light, and the health sensor can be an infrared sensor correspondingly. Certainly, when the health sensor is an infrared sensor, since the fingerprint sensor is configured to collect visible light, the fingerprint sensor cannot be reused as a health sensor.

The health parameter information obtained by the optical fingerprint module of the present disclosure may include any of the following: heart rate, blood oxygen and blood pressure. Certainly, the above is only an example and illustrative. It should be understood that any parameter that can reflect the state of health can be used as the health parameter information of the present disclosure. The specific health parameter information obtained is related to the processing method of the health signal, which is not limited in the present disclosure.

The control unit in the present disclosure may be an MCU (Microcontroller Unit), a DSP (digital signal processor), or a CPU (central processing unit). Certainly, the above is only an example and illustrative. It should be understood that the hardware that can generate the health parameter information based on the health signal and can generate the fingerprint information for the fingerprint recognition based on the fingerprint signal can be used as the aforementioned control unit, which is not limited in the present disclosure It can be seen from the above technical solutions that the optical fingerprint module according to embodiments of the present disclosure has both the health testing function and the fingerprint recognition function. Therefore, when this optical fingerprint module is integrated to an electronic device, there is no need to arrange a separate health sensor, thereby solving the problem existing in the related arts that the ratio of the area of the screen to the area of the front panel of the electronic device is reduced or the mechanical strength of the backplane of the electronic device is reduced by separately arranging the health sensor.

In addition, with the above-mentioned optical fingerprint module, since there is no need to arrange the health sensor separately, the space of the main circuit board of electronic device that is occupied by the health sensor may be reduced, such that developers can flexibly arrange various components at desired positions on the main circuit board, and development difficulty may be reduced.

Further, the health sensor according to the present disclosure can include both the red light sensor and the green light sensor. In this case, a signal that is less interfered may be selected from the signal collected by the red light sensor and the signal collected by the green light sensor can be selected to generate the health parameter information, thereby improving the accuracy of the health testing.

Figure 10:
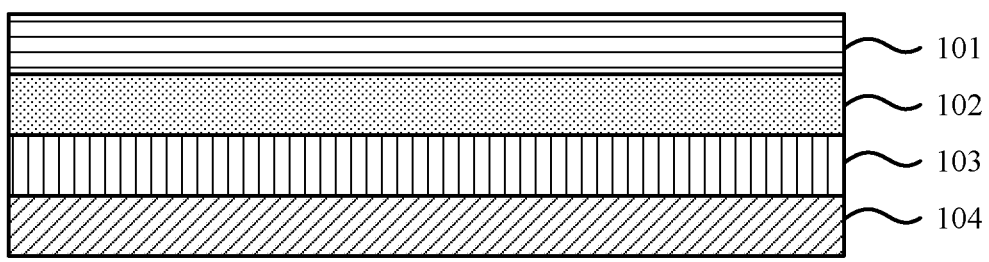
FIG. 10 is a schematic diagram illustrating a touch display module according to some embodiments of the present disclosure.

FIG. 10 is a schematic diagram illustrating a touch and display module according to some embodiments of the present disclosure. As illustrated in FIG. 10, the touch and display module includes a glass cover layer 101, a touch layer 102, a display layer 103, and a health testing and fingerprint recognition layer 104.

A sensing side of the touch layer 102 faces towards the glass cover layer 101.

A light-emitting side of the display layer 103 faces towards a non-sensing side of the touch layer 102.

The health testing and fingerprint recognition layer 104 includes the optical fingerprint module as described above, and a light-incoming side of the health testing and fingerprint recognition layer 104 faces towards the non-light-emitting side of the display layer 103.

The glass cover layer 101 may be made of a transparent glass material for protecting the touch and display module. The sensing side of the touch layer 102 can generate a touch signal based on a user's touch position. The method for generating the touch signal can be a sensing method of a capacitive screen or a sensing method of a resistive screen, which is not limited herein. The display layer 103 is also called a light-emitting layer and can display a corresponding image based on a control signal. The light sensing unit of the optical fingerprint module may be arranged on the light-incoming side of the health testing and fingerprint recognition layer 104 to collect the light signals.

It can be seen from the above touch display module that the health testing and fingerprint recognition layer of the touch and display module includes the optical fingerprint module described above. It can be seen that the processes of the health testing and fingerprint recognition are both performed by the touch and display module, such that the electronic device using the touch and display module does not need to arrange a separate health sensor. Compared to the electronic device that has a separately arranged health sensor outside the touch and display module, the mechanical strength of the backplane of the electronic device may be not affected and the ratio of the area of the screen to the area of the front panel may be higher in the present disclosure.

Figure 11:
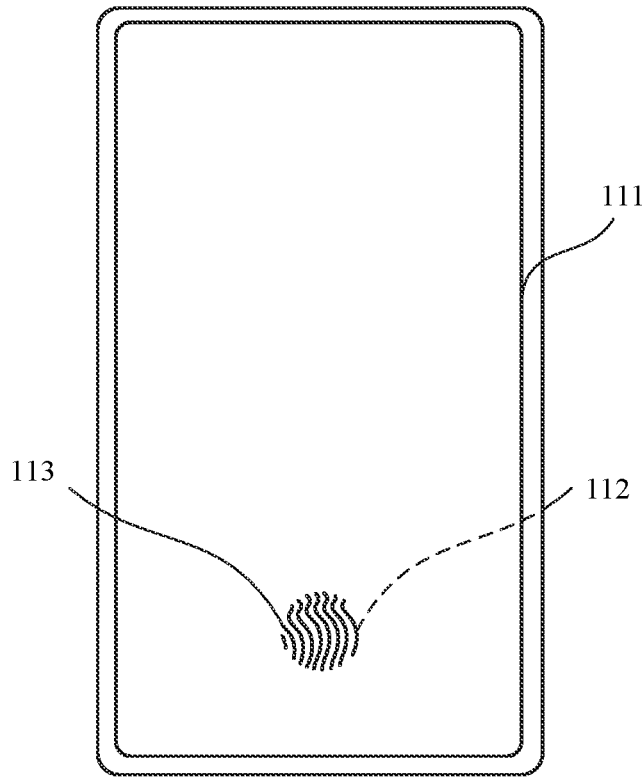
FIG. 11 is a schematic structural diagram of an electronic device equipped with an optical fingerprint module according to some embodiments of the present disclosure.

FIG. 11 is a schematic diagram illustrating an electronic device according to some embodiments of the present disclosure. As illustrated in FIG. 11, the electronic device includes: a touch and display module 111 and the optical fingerprint module 112 as described above. The assembly position of the optical fingerprint module corresponds to the fingerprint recognition region 113 formed on the touch and display module; or the electronic device includes the touch and display module as illustrated in FIG. 10.

In some embodiments, the user can touch the fingerprint recognition region 113 with a finger to trigger the electronic device to perform the fingerprint recognition operation.

In actual operations, in order to accurately detect the user's fingerprints, several fingerprint sensors may be regularly distributed in the optical fingerprint module 112. In one case, at least one of the fingerprint sensors can be used as the health sensor of the optical fingerprint module. In this case, the fingerprint sensor may be reused as a health sensor, that is, the fingerprint sensor is also functioned as the health sensor and is configured to perform the fingerprint recognition and the health testing, thereby reducing the number of sensors to be deployed. In another case, a health sensor can be arranged near at least one fingerprint sensor. In this case, compared to the layout in the related arts, the position of the health sensor moves from outside the touch and display module to the fingerprint recognition region of the touch and display module, thereby avoiding separately arranging a health sensor.

In the electronic device according to embodiments of the present disclosure, the optical fingerprint module described above is assembled in the fingerprint recognition region. It can be seen that both the fingerprint sensor and the health sensor are arranged in the touch and display module, which solves the problem that the ratio of the area of the screen to the area of the front panel of the electronic device is reduced and the mechanical strength of the backplane of the electronic device is reduced due to the separately arranged health sensor.

Figure 12:
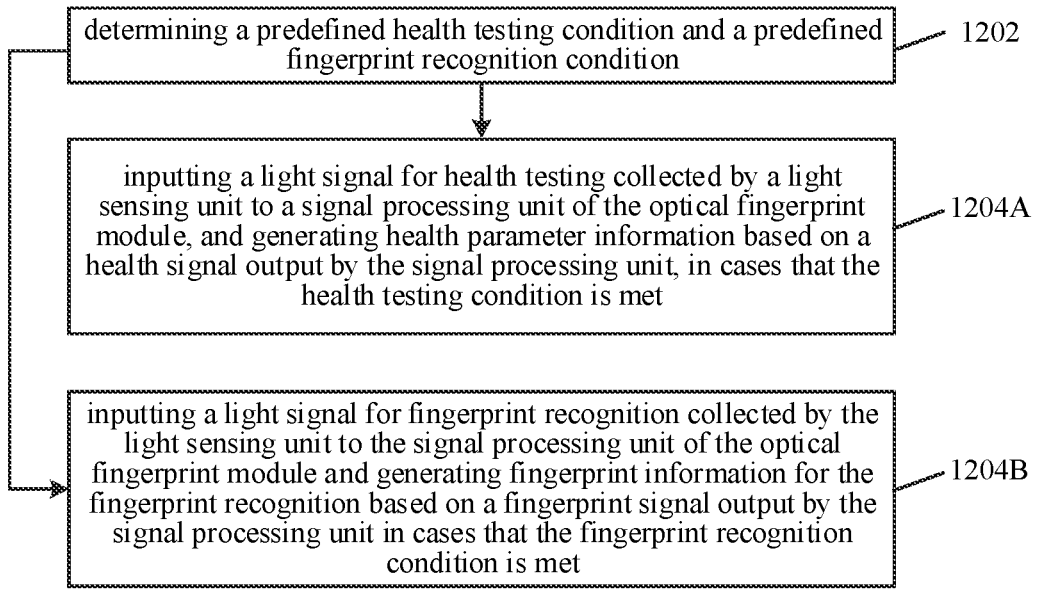
FIG. 12 is a flowchart illustrating a method for processing a signal according to some embodiments of the present disclosure.

FIG. 12 is a flowchart illustrating a method for processing a signal according to some embodiments of the present disclosure. The method is applied to an electronic device including the optical fingerprint module as described above, or an electronic device as described above. The method may include the following.

At block 1202, a predefined health testing condition and a predefined fingerprint recognition condition are determined.

In some embodiments, after the light signals are collected by the light sensing unit in the optical fingerprint module, it can be determined whether to perform the health monitoring or the fingerprint recognition to collect corresponding light signals by the light sensing unit, based on the predefined health testing condition and the predefined fingerprint recognition condition.

At block 1204A, when the health testing condition is met, the light signals for the health testing collected by the light sensing unit is input to the signal processing unit in the optical fingerprint module, to generate the health parameter information based on the health signal output by the signal processing unit.

At block 1204B, when the fingerprint recognition condition is met, the light signals for the fingerprint recognition collected by the light sensing unit is input to the signal processing unit in the optical fingerprint module, to generate the fingerprint information for the fingerprint recognition based on the fingerprint signal output by the signal processing unit.

In practical applications, when the user's finger touches the fingerprint recognition region, the fingerprint recognition is usually performed to perform operations such as unlocking and payment. Therefore, it can be determined whether the fingerprint recognition is required by determining whether the fingerprint recognition region formed by the touch and display module of the electronic device detects a touch event or not. In this case, when a touch event that occurs in the fingerprint recognition region is detected, it is determined that the fingerprint recognition condition is met.

However, in actual situations, it is inevitable that there will be false touches. Therefore, on the premise of the aforementioned fingerprint recognition condition, that is, in the case that the touch event occurring in the fingerprint recognition region is detected, it can be further determined whether a pressing force corresponding to the touch event is not less than a preset pressure threshold. In the case that the pressing force is not less than the preset pressure threshold, it is determined that the fingerprint recognition condition is satisfied.

It should be understood that when a user desires to perform the health testing, the user usually launches an application related to the health testing in the electronic device, and activate the corresponding health testing function of the application. Therefore, in the present disclosure, a function of realizing the health testing may be set as a preset function and it may be determined whether the preset function of the electronic device is in an on state during the operation of the electronic device. In response to detecting that the preset function is in the on state, it is determined that the health detection condition is satisfied.

In practical applications, after the light used for health detection is collected, different software processing methods are adopted for the light to obtain different health parameter information. For example, the heart rate, blood oxygen, blood pressure and other parameters of the subject can be obtained by processing and analyzing the collected light.

It can be seen from the above technical solutions that, through the electronic device equipped with the optical fingerprint module, the light signals used to generate the health signal and the fingerprint signal are collected by the sensor arranged in the touch and display module, thereby solving the problem existing in the related arts that the ratio of the area of the screen to the area of the front panel of the electronic device is reduced and the mechanical strength of the backplane of the electronic device is affected by separately arranging the health sensor.

Further, in embodiments of the present disclosure, by determining whether the fingerprint recognition region is touched, it may be determined whether the fingerprint recognition is currently required. It should be understood that touching the fingerprint recognition region by the user means that there are unlocking and payment requirements, and fingerprint recognition is required. In the present disclosure, whether the preset function is in the on state is also used as the health detection condition. It should be understood that when the user activates the preset function for realizing the health testing, it is obviously that there is a need for the health testing. Thus, the technical solutions according to the present disclosure can perform the health testing or the fingerprint recognition based on the actual needs of the user, thereby improving user experience.

Figure 13:
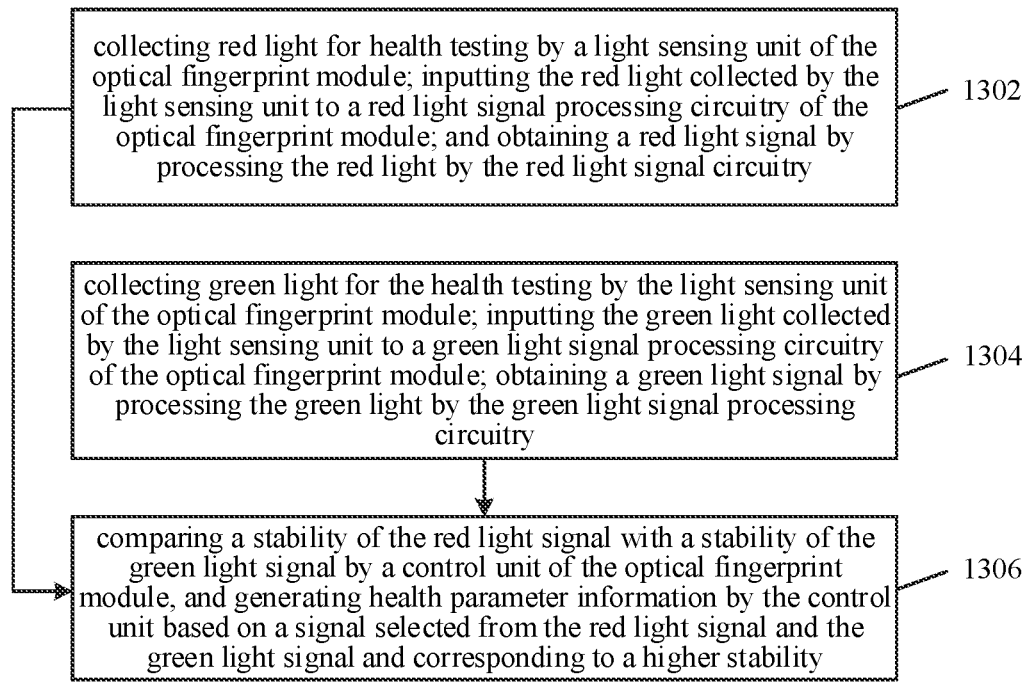
FIG. 13 is a flowchart illustrating a method for health testing according to some embodiments of the present disclosure.

FIG. 13 is a flowchart illustrating a method for health testing according to some embodiments of the present disclosure. The method is applicable to an electronic device including the optical fingerprint model having both a red light collecting function and a green light collecting function as described above. The method can include the following.

At block 1302, the red light for the health testing is collected by the light sensing unit in the optical fingerprint module, and the red light collected by the light sensing unit is inputted into the red light signal processing circuitry in the optical fingerprint module, such that the red light signal processing circuitry processes the red light to obtain the red light signal.

At step 1304, the green light for the health testing is collected by the light sensing unit in the optical fingerprint module, and the green light collected by the light sensing unit is input into the green light signal processing circuitry in the optical fingerprint module, such that the green light signal processing circuitry processes the green light to obtain the green light signal.

It should be understood that since the light may be interfered by many factors during the propagation process, the light will continuously change during the propagation process. In addition, there are certain differences in interfering different lights in different environments. That is, the stabilities of different lights are different in different environments. For example, when the human body is sweating, the sweat is easier to absorb the green light than the red light. As a result, the red light is more stable when the human body is sweating, and health testing is more accurate based on the red light. In view of this, in embodiments, the red light and the green light are collected by the optical fingerprint module, and the stability of the red light signal obtained by processing the red light is compared with the stability of the green light signal obtained by processing the green light to select the a signal having the higher stability as the health signal to generate the health parameter information.

In addition, normally, since the green light is better absorbed by the human body, changes in the human body may be easier detected based on the green light, and the health testing based on the green light may be more accurate. Therefore, in some embodiments, if the stability of the red light signal obtained by processing the red light is close to that of the green light signal obtained by processing the green light, the health testing is performed based on the green light signal obtained by processing the green light.

In some embodiments, the optical fingerprint module provided in the electronic device requires the functions of collecting the red light and the green light. Therefore, the optical fingerprint module according to the embodiments may be an optical fingerprint module being capable of collecting the red light and the green light as described above.

At block 1306, the stability of the red light signal is compared with the stability of the green light signal by the control unit in the optical fingerprint module, such that the control unit may generate the health parameter information based on a signal having the higher stability and selected from the red light signal and the green light signal.

In some embodiments, the health testing is performed with the red light and the green light. It is usually necessary to configure corresponding light emitting ends, such as the red light emitting end in the electronic device and configured to emit the red light, and the green light emitting end in the electronic device and configured to emit the green light. Certainly, since the optical fingerprint module in the electronic device can emit light itself, the red light and/or green light used for the health testing can be emitted by the optical fingerprint module.

In some embodiments, the obtained health parameter information may include any of: heart rate, blood oxygen, and blood pressure. Certainly, the above is only an example and illustrative. It should be understood that any parameter that can reflect the state of health can be used as the health parameter information of the present disclosure. The specific health parameter information obtained is related to the method for processing the health signal, which is not limited in the present disclosure.

It can be seen from the above technical solutions that by collecting the red light and the green light for the health testing through the optical fingerprint module, and comparing the red light signal obtained by processing the red light and the green light signal obtained by processing the green light, the health parameter information may be generated based on the signal having the higher stability. In other words, the accuracy of health testing may be improved in the present disclosure by selecting the better one from the red light signal and the green light signal.

Corresponding to the foregoing embodiments of the method for processing a signal, the present disclosure also provides embodiments of a device for processing a signal.

Figure 14:
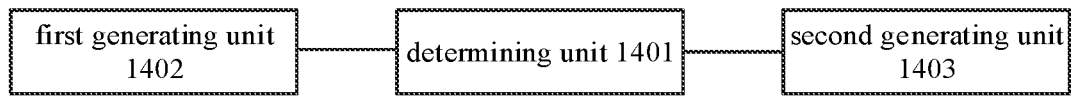
FIG. 14 is a block diagram illustrating a device for processing a signal according to some embodiments of the present disclosure.

FIG. 14 is a block diagram illustrating a device for processing a signal according to some embodiments of the present disclosure. As illustrated in FIG. 14, the device may include a determining unit 1401, a first generating unit 1402, and a second generating unit 1403.

The determining unit 1401 is configured to determine a predefined health testing condition and a predefined fingerprint recognition condition.

The first generating unit 1402 is configured to input the light signal for the health testing collected by the light sensing unit to the signal processing unit in the optical fingerprint module when the health testing condition is satisfied, and to generate the health parameter information based on the health signal output by the signal processing unit.

The second generating unit 1403 is configured to input the light signal for the fingerprint recognition collected by the light sensing unit to the signal processing unit in the optical fingerprint module when the fingerprint recognition condition is satisfied, to generate the fingerprint information for the fingerprint recognition based on the fingerprint signal output by the signal processing unit.

Figure 15:
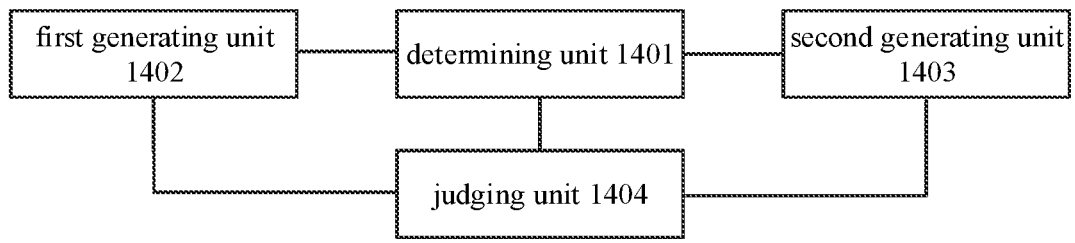
FIG. 15 is a block diagram illustrating another device for processing a signal according to some embodiments of the present disclosure.

As illustrated in FIG. 15, FIG. 15 is a block diagram illustrating another device for processing a signal processing device according to some embodiments of the present disclosure. On the basis of the foregoing embodiment illustrated in FIG. 14, this embodiment further includes a judging unit 1404.

The judging unit 1404 is configured to determine whether a touch event is detected in the fingerprint recognition region formed by the touch and display module of the electronic device.

Meeting the fingerprint recognition condition includes detecting that the touch event occurs in the fingerprint recognition region.

In some embodiments, meeting the fingerprint recognition condition further includes: in the case of detecting that the touch event occurs in the fingerprint recognition region, determining that a pressing force corresponding to the touch event is not less than a preset pressure threshold.

In some embodiments, the judging unit 1404 is further configured to determine whether the preset function of the electronic device is in an on state.

Meeting the health testing condition includes that the preset function is in the on state.

It should be noted that the judging unit 1404 in the device embodiments illustrated in FIG. 15 may also be included in the device embodiment in FIG. 14, which is not limited in the present disclosure.

Corresponding to the foregoing embodiment of the method for acquiring a health signal, the present disclosure also provides embodiments of a device for acquiring a health signal.

Figure 16:
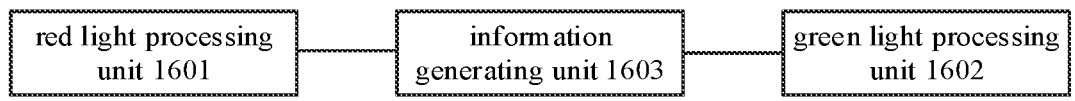
FIG. 16 is a block diagram illustrating a device for health testing according to some embodiments of the present disclosure.

FIG. 16 is a block diagram illustrating a device for acquiring a health signal according to some embodiments of the present disclosure. As illustrated in FIG. 16, the device may include a red light processing unit 1601, a green light processing unit 1602, and an information generating unit 1603.

The red light processing unit 1601 is configured to collect the red light for the health testing by the light sensing unit in the optical fingerprint module; input the red light collected by the light sensing unit into the red light signal processing circuitry of the optical fingerprint module; and process the red light by the red light signal processing circuitry to obtain the red light signal.

The green light processing unit 1602 is configured to collect the green light for the health testing by the light sensing unit in the optical fingerprint module; input the green light collected by the light sensing unit into the green light signal processing circuitry of the optical fingerprint module; and process the green light by the green light signal processing circuitry to obtain the green light signal.

The information generating unit 1603 is configured to compare the stability of the red light signal and the stability of the green light signal by the control unit of the optical fingerprint module, and generate the health parameter information by the control unit based on a signal having the higher stability and selected from the red light signal and the green light signal.

In some embodiments, the red light and/or the green light are emitted by a touch and display module of the electronic device.

In some embodiments, the red light is emitted by the red light emitting end of the electronic device; and the green light is emitted by the green light emitting end of the electronic device.

In some embodiments, the health parameter information includes at least one of: value of heart rate, value of blood oxygen, and value of blood pressure.

Regarding the device in the foregoing embodiments, the specific manner in which each module performs operations has been described in detail in the embodiments of the method, and detailed description will not be given here.

As for the device embodiments, since they basically correspond to the method embodiments, the relevant part can refer to the part of the description of the method embodiments. The device embodiments described above are merely illustrative. The units described as separate components may or may not be physically separated, and the components displayed as units may or may not be physical units, that is, they may be located in one place, or distributed to multiple network units. Some or all of the modules can be selected according to actual needs to achieve the objectives of the technical solutions of the present disclosure. Those of ordinary skill in the art can understand and implement it without creative work.

Correspondingly, the present disclosure also provides a device for processing a signal, including: a processor and a memory. The memory is configured to store instructions executable by the processor. The processor is configured to implement the method for processing a signal as described in any of the above embodiments. For example, the method may include determining a predefined health testing condition and a predefined fingerprint recognition condition; when the health testing condition is met, inputting the light signal for the health testing collected by the light sensing unit to the signal processing unit of the optical fingerprint module described herein, and generating the health parameter information based on the health signal output by the signal processing unit; when the fingerprint recognition condition is met, inputting the light signal for the fingerprint recognition collected by the light sensing unit to the signal processing unit of the optical fingerprint module described above, and generating the fingerprint information for the fingerprint recognition based on the fingerprint signal output by the signal processing unit.

In some embodiments, the processor is configured to determine a pre-defined health testing condition and a pre-defined fingerprint recognition condition; generate a health signal based on a light signal for health testing, and generate health parameter information based on the health signal, in cases that the health testing condition is met; and generate a fingerprint signal based on a light signal for fingerprint recognition, and generate fingerprint information for the fingerprint recognition based on the fingerprint signal in cases that the fingerprint recognition condition is met Correspondingly, the present disclosure also provides a device for acquiring a health signal including a processor and a memory. The memory is configured to store instructions executable by the processor. The processor is configured to implement the method for acquiring a health signal according to any one of the above-mentioned embodiments. For example, the method may include: collecting red light for the health testing by a light sensing unit of the optical fingerprint module; inputting the red light collected by the light sensing unit into the aforementioned red light signal processing circuitry of the optical fingerprint module with the red light collection function and the green light collection function, and processing the red light by the red light signal processing circuitry to obtain the red light signal; collecting green light for the health testing by the light sensing unit of the optical fingerprint module; inputting the green light collected by the light sensing unit into the green light signal processing circuitry in the optical fingerprint module with the red light collection function and the green light collection function described above, and processing the green light by the green light signal processing circuitry to obtain the green light signal; comparing by the control unit in the optical fingerprint module the stability of the red light signal and the stability of the green light signal, and generating the health parameter information by the control unit based on a signal selected from the red light signal and the green light signal and corresponding to the higher stability.

In some embodiments, the processor is configured to obtain a red light signal based on red light for health testing; obtain a green light signal based on green light for health testing; compare a stability of the red light signal with a stability of the green light signal; and generate health parameter information based on a signal selected from the red light signal and the green light signal and corresponding to a higher stability.

Correspondingly, the present disclosure also provides an electronic device including a memory and one or more programs. The one or more programs are stored in the memory and are configured such that the one or more processors execute instructions for implementing the method for processing a signal or the method for acquiring a health signal as described in any of the above embodiments. For example, the method may include: determining a predefined health testing condition and a fingerprint recognition condition; in the case that the health testing condition is met, inputting the light signal for the health testing collected by the light sensing unit to the signal processing unit in the optical fingerprint module described above, to generate the health parameter information based on the health signal output by the signal processing unit; in the case that the fingerprint recognition condition is met, inputting the light signal for the fingerprint recognition collected by the light sensing unit into the signal processing unit of the optical fingerprint module described above, to generate the fingerprint information for the fingerprint recognition based on the fingerprint signal output by the signal processing unit.

Figure 17:
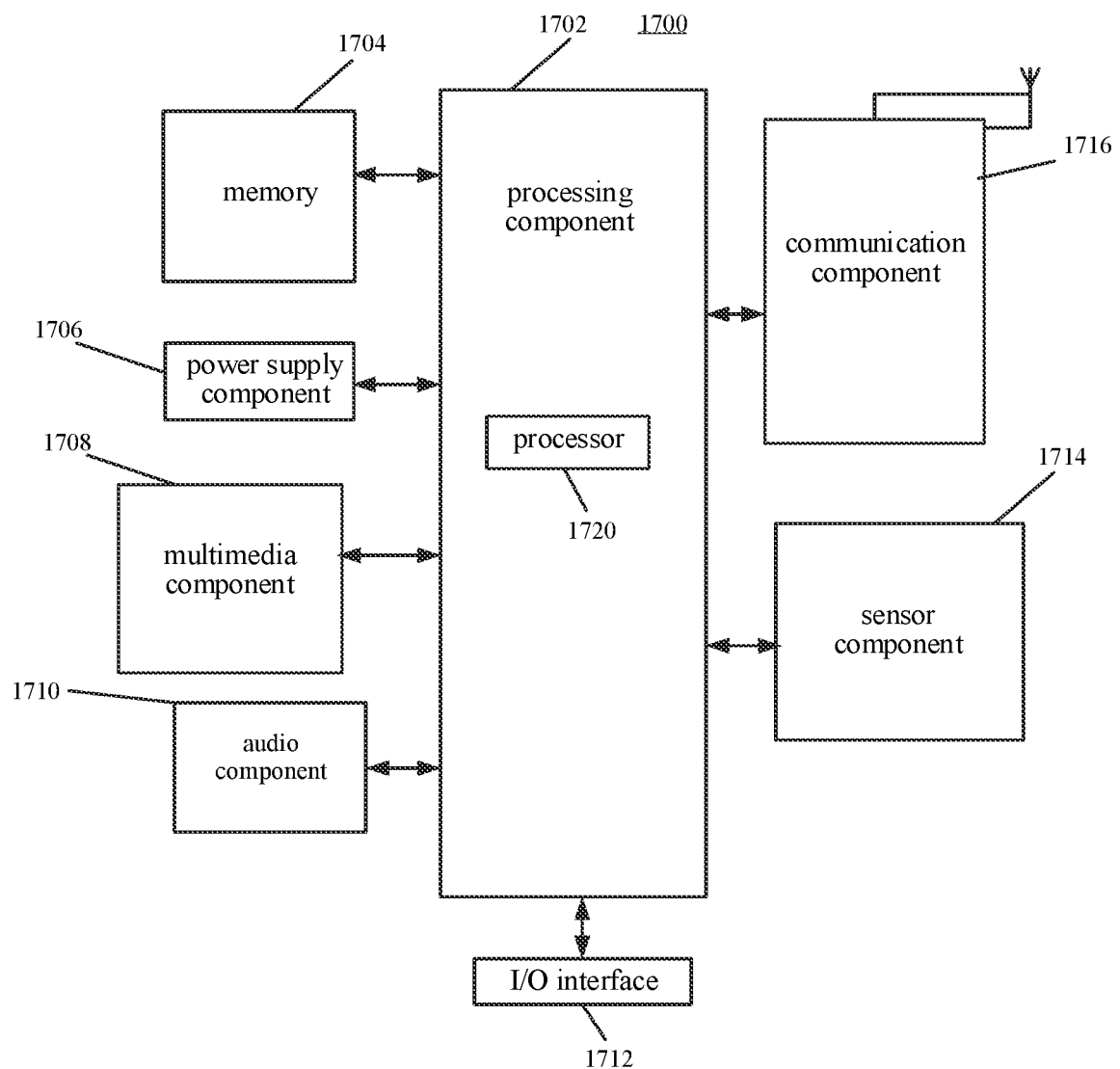
FIG. 17 is a block diagram illustrating a device for implementing a method for processing a signal according to some embodiments of the present disclosure.

FIG. 17 is a block diagram illustrating a device 1700 for implementing a method for processing a signal according to some embodiments of the present disclosure. For example, the device 1700 may be a mobile phone, a computer, a digital broadcasting terminal, a messaging device, a game console, a tablet device, a medical device, a fitness device, a personal digital assistant, etc.

As illustrated in FIG. 17, the device 1700 may include one or more of: a processing component 1702, a memory 1704, a power supply component 1706, a multimedia component 1708, an audio component 1710, an input/output (I/O) interface 1712, a sensor component 1714, and a communication component 1716.

The processing component 1702 generally controls the overall operations of the device 1700, such as operations associated with display, calls, data communications, camera operations, and recording operations. The processing component 1702 may include one or more processors 1720 to execute instructions to complete all or part of the steps of the foregoing method. In addition, the processing component 1702 may include one or more modules to facilitate the interaction between the processing component 1702 and other components. For example, the processing component 1702 may include a multimedia module to facilitate the interaction between the multimedia component 1708 and the processing component 1702.

The memory 1704 is configured to store various types of data to support operations of the device 1700. Examples of such data include instructions for any application or method operating on the device 1700, contact data, phone book data, messages, pictures, videos, etc. The memory 1704 can be implemented by any type of volatile or non-volatile storage devices or the combination thereof, such as static random access memory (SRAM), electrically erasable programmable read-only memory (EEPROM), erasable Programmable read-only memory (EPROM), programmable read-only memory (PROM), read-only memory (ROM), magnetic memory, flash memory, magnetic disk or optical disk.

The power supply component 1706 provides power to various components of the device 1700. The power supply component 1706 may include a power management system, one or more power supplies, and other components associated with the generation, management, and distribution of power for the device 1700.

The multimedia component 1708 includes a screen that provides an output interface between the device 1700 and the user. In some embodiments, the screen may include a liquid crystal display (LCD) and a touch panel (TP). If the screen includes a touch panel, the screen may be implemented as a touch screen to receive input signals from the user. The touch panel includes one or more touch sensors to sense touch, sliding, and gestures on the touch panel. The touch sensor may not only sense the boundary of a touch or a slide action, but also detect the duration and pressure related to the touch or the slide operation. In some embodiments, the multimedia component 1708 includes a front camera and/or a rear camera. When the device 1700 is in an operation mode, such as a shooting mode or a video recording mode, the front camera and/or the rear camera can receive external multimedia data. Each front camera and rear camera can be a fixed optical lens system or have focal length and optical zoom capabilities.

The audio component 1710 is configured to output and/or input audio signals. For example, the audio component 1710 includes a microphone (MIC). When the device 1700 is in an operating mode, such as a call mode, a recording mode, and a voice recognition mode, the microphone is configured to receive external audio signals. The received audio signal may be further stored in the memory 1704 or transmitted via the communication component 1716. In some embodiments, the audio component 1710 further includes a speaker for outputting audio signals.

The I/O interface 1712 provides an interface between the processing component 1702 and a peripheral interface module. The peripheral interface module may be a keyboard, a click wheel, a button, and the like. These buttons may include but are not limited to home button, volume button, start button, and lock button.

The sensor component 1714 includes one or more sensors for providing the device 1700 with various aspects of status assessment. For example, the sensor component 1714 can detect the opening/closing status of the device 1700 and the relative positioning of components. For example, the component is the display and the keypad of the device 1700. The sensor component 1714 can also detect the position change of the device 1700 or a component of the device 1700, the presence or absence of contact between the user and the device 1700, the orientation or acceleration/deceleration of the device 1700, and the temperature change of the device 1700. The sensor assembly 1714 may include a proximity sensor configured to detect the presence of nearby objects when there is no physical contact. The sensor component 1714 may also include a light sensor, such as a CMOS or CCD image sensor, for use in imaging applications. In some embodiments, the sensor component 1714 may also include an acceleration sensor, a gyroscope sensor, a magnetic sensor, a pressure sensor or a temperature sensor.

The communication component 1716 is configured to facilitate wired or wireless communication between the device 1700 and other devices. The device 1700 can access a wireless network based on a communication standard, such as WiFi, 2G or 3G 4G LTE, 5G NR (new radio), or a combination thereof. In an exemplary embodiment, the communication component 1716 receives a broadcast signal or broadcast-related information from an external broadcast management system via a broadcast channel. In an exemplary embodiment, the communication component 1716 further includes a near field communication (NFC) module to facilitate short-range communication. For example, the NFC module can be implemented based on radio frequency identification (RFID) technology, infrared data association (IrDA) technology, ultra-wideband (UWB) technology, Bluetooth (BT) technology and other technologies.

In an exemplary embodiment, the apparatus 1700 may be implemented by one or more application specific integrated circuits (ASIC), digital signal processors (DSP), digital signal processing equipment (DSPD), programmable logic devices (PLD), field programmable Implemented by a gate array (FPGA), controller, microcontroller, microprocessor, or other electronic components, used to perform the above methods.

In some embodiments, there is also provided a non-transitory computer-readable storage medium including instructions, such as a memory 1704 including instructions, which can be executed by the processor 1720 of the device 1700 to implement the foregoing method. For example, the non-transitory computer-readable storage medium may be ROM, random access memory (RAM), CD-ROM, magnetic tape, floppy disk, optical data storage device, etc.

After considering the specification and practicing the disclosure disclosed herein, those skilled in the art will easily obtain other embodiments of the present disclosure. The present disclosure is intended to cover any variations, uses, or adaptive changes of the present disclosure. These variations, uses, or adaptive changes follow the general principles of the present disclosure and include common knowledge or conventional technical means in the technical field not disclosed in the present disclosure. The description and the embodiments are only regarded as exemplary, and the true scope and spirit of the present disclosure are pointed out by the following claims.

It should be understood that the present disclosure is not limited to the precise structure that has been described above and shown in the drawings, and various modifications and changes can be made without departing from its scope. The scope of the present disclosure is only limited by the appended claims.

The above are only the preferred embodiments of the present disclosure and are not intended to limit the present disclosure. Any modification, equivalent replacement, improvement, etc. made within the spirit and principle of the present disclosure shall be included in the present disclosure within the scope of protection.

What is claimed is:

1. An optical fingerprint module, comprising:
a light sensing unit, configured to collect a light signal;
a signal processing unit, connected to the light sensing unit and configured to generate at least one of a fingerprint signal and a health signal by processing the light signal collected by the light sensing unit; and
a control unit, connected to the signal processing unit and configured to generate fingerprint information for fingerprint recognition based on the fingerprint signal output by the signal processing unit and generate health parameter information based on the health signal output by the signal processing unit;
wherein, the light sensing unit comprises a fingerprint sensor, in which the fingerprint sensor is configured to collect the light signal for the fingerprint recognition and further configured to collect at least one of red light and green light for health testing;
the signal processing unit comprises:
a fingerprint signal processing circuitry, connected to the control unit and configured to obtain the fingerprint signal by processing the light signal collected by the fingerprint sensor; and at least one of:
a red light signal processing circuitry, connected to the control unit and configured to obtain a red light signal by processing the red light collected by the fingerprint sensor; and a green light signal processing circuitry, connected to the control unit and configured to obtain a green light signal by processing the green light collected by the fingerprint sensor; and
the optical fingerprint module further comprises:
a first circuit gating switch, configured to directly connect the fingerprint sensor to the fingerprint signal processing circuitry in response to the light signal collected by the fingerprint sensor is visual light signal, directly connect the fingerprint sensor to the red light signal processing circuitry in response to the light signal collected by the fingerprint sensor is red light signal, and directly connect the fingerprint sensor to the green light signal processing circuitry in response to the light signal collected by the fingerprint sensor is green light signal; and
the control unit is configured to generate the fingerprint information for the fingerprint recognition based on the fingerprint signal output by the fingerprint signal processing circuitry, generate the health parameter information based on the red light signal output by the red light signal processing circuitry, or generate the health parameter information based on the green light signal output by the green light signal processing circuitry.

2. The optical fingerprint module according to claim 1, wherein,
the light sensing unit comprises:
a fingerprint sensor, configured to collect a first light signal for the fingerprint recognition; and
a health sensor configured to collect a second light signal for health testing;
the signal processing unit comprises:
a fingerprint signal processing circuitry, connected to the fingerprint sensor and configured to obtain the fingerprint signal by processing the first light signal collected by the fingerprint sensor; and
a health signal processing circuitry, configured to obtain the health signal by processing the second light signal collected by the health sensor; and
the control unit is connected to both the fingerprint signal processing circuitry and the health signal processing circuitry and configured to generate the fingerprint information for the fingerprint recognition based on the fingerprint signal output by the fingerprint signal processing circuitry and generate the health parameter information based on the health signal output by the health signal processing circuitry.

3. The optical fingerprint module according to claim 2, wherein,
the health sensor comprises at least one of:
a red light sensor, configured to collect red light for the health testing; and
a green light sensor, configured to collect green light for the health testing;

the health signal processing circuitry comprises at least one of:
a red light signal processing circuitry, connected to the red light sensor and configured to obtain a red light signal by processing the red light collected by the red light sensor; and
a green light signal processing circuitry, connected to the green light sensor and configured to obtain a green light signal by processing the green light collected by the green light sensor;
the control unit is connected to the fingerprint signal processing circuitry and configured to generate the fingerprint information for the fingerprint recognition based on the fingerprint signal output by the fingerprint signal processing circuitry; the control unit is further connected to at least one of the red light signal processing circuitry and the green light signal processing circuitry and configured to generate the health parameter information based on at least one of the red light signal output by the red light signal processing circuitry and the green light signal output by the green light signal processing circuitry.

4. The optical fingerprint module according to claim 1, wherein,
the light sensing unit comprises:
a first fingerprint sensor, configured to collect a first light signal for the fingerprint recognition and red light for health testing, and
a second fingerprint sensor, configured to collect a second light signal for the fingerprint recognition and green light for health testing;
the signal processing unit comprises:
a first fingerprint signal processing circuitry, connected to the control unit and configured to obtain a first fingerprint signal by processing the first light signal collected by the first fingerprint sensor;
a red light signal processing circuitry, connected to the control unit and configured to obtain a red light signal by processing the red light collected by the first fingerprint sensor;
a second fingerprint signal processing circuitry, connected to the control unit and configured to obtain a second fingerprint signal by processing the second light signal collected by the second fingerprint sensor; and
a green light signal processing circuitry, connected to the control unit and configured to obtain a green light signal by processing the green light collected by the second fingerprint sensor;
the optical fingerprint module further comprises:
a second circuit gating switch, in which one terminal of the second circuit gating switch is connected to the first fingerprint sensor, and the other terminal of the second circuit gating switch is connected to either the first fingerprint signal processing circuitry or the red light signal processing circuitry; and
a third circuit gating switch, in which one terminal of the third circuit gating switch is connected to the second fingerprint sensor, and the other terminal of the third circuit gating switch is connected to either the second fingerprint signal processing circuitry or the green light signal processing circuitry;
the control unit is configured to:
generate the fingerprint information for the fingerprint recognition based on at least one of the first fingerprint signal output by the first fingerprint signal processing circuitry and the second fingerprint signal output by the second fingerprint signal processing circuitry; and
generate the health parameter information based on at least one of the red light signal output by the red light signal processing circuitry and the green light signal output by the green light signal processing circuitry.

5. The optical fingerprint module according to claim 3, further comprising at least one of:
a red light emitting end, configured to emit the red light for the health testing; and
a green light emitting end, configured to emit the green light for the health testing.

6. The optical fingerprint module according to claim 1, wherein the health parameter information comprises at least one of:
value of heart rate, value of blood oxygen, and value of blood pressure.

7. An electronic device, comprising:
a touch and display module and an optical fingerprint module, wherein an assembly position of the optical fingerprint module corresponds to a fingerprint recognition region formed on the touch and display module; and the optical fingerprint module comprises:
a light sensing unit, configured to collect a light signal;
a signal processing unit, connected to the light sensing unit and configured to generate at least one of a fingerprint signal and a health signal by processing the light signal collected by the light sensing unit; and
a control unit, connected to the signal processing unit and configured to generate fingerprint information for fingerprint recognition based on the fingerprint signal output by the signal processing unit and generate health parameter information based on the health signal output by the signal processing unit;
wherein the light sensing unit comprises a fingerprint sensor, in which the fingerprint sensor is configured to collect the light signal for the fingerprint recognition and further configured to collect at least one of red light and green light for health testing;
the signal processing unit comprises:
a fingerprint signal processing circuitry, connected to the control unit and configured to obtain the fingerprint signal by processing the light signal collected by the fingerprint sensor; and at least one of:
a red light signal processing circuitry, connected to the control unit and configured to obtain a red light signal by processing the red light collected by the fingerprint sensor; and a green light signal processing circuitry, connected to the control unit and configured to obtain a green light signal by processing the green light collected by the fingerprint sensor; and
the optical fingerprint module further comprises:
a first circuit gating switch, configured to directly connect the fingerprint sensor to the fingerprint signal processing circuitry in response to the light signal collected by the fingerprint sensor is visual light signal, directly connect the fingerprint sensor to the red light signal processing circuitry in response to the light signal collected by the fingerprint sensor is red light signal, and directly connect the fingerprint sensor to the green light signal processing circuitry in response to the light signal collected by the fingerprint sensor is green light signal; and the control unit is configured to generate the fingerprint information for the fingerprint recognition based on the fingerprint signal output by the fingerprint signal processing circuitry, generate the health parameter information based on the red light signal output by the red light signal processing circuitry, or generate the health parameter information based on the green light signal output by the green light signal processing circuitry.

8. The electronic device according to claim 7, wherein, the light sensing unit comprises:
   a fingerprint sensor, configured to collect a first light signal for the fingerprint recognition; and
   a health sensor configured to collect a second light signal for health testing;
the signal processing unit comprises:
   a fingerprint signal processing circuitry, connected to the fingerprint sensor and configured to obtain the fingerprint signal by processing the first light signal collected by the fingerprint sensor; and
   a health signal processing circuitry, configured to obtain the health signal by processing the second light signal collected by the health sensor; and
the control unit is connected to both the fingerprint signal processing circuitry and the health signal processing circuitry and configured to generate the fingerprint information for the fingerprint recognition based on the fingerprint signal output by the fingerprint signal processing circuitry and generate the health parameter information based on the health signal output by the health signal processing circuitry.

9. The electronic device according to claim 8, wherein, the health sensor comprises at least one of:
   a red light sensor, configured to collect red light for the health testing; and
   a green light sensor, configured to collect green light for the health testing;
the health signal processing circuitry comprises at least one of:
   a red light signal processing circuitry, connected to the red light sensor and configured to obtain a red light signal by processing the red light collected by the red light sensor; and
   a green light signal processing circuitry, connected to the green light sensor and configured to obtain a green light signal by processing the green light collected by the green light sensor;
the control unit is connected to the fingerprint signal processing circuitry and configured to generate the fingerprint information for the fingerprint recognition based on the fingerprint signal output by the fingerprint signal processing circuitry; the control unit is further connected to at least one of the red light signal processing circuitry and the green light signal processing circuitry and configured to generate the health parameter information based on at least one of the red light signal output by the red light signal processing circuitry and the green light signal output by the green light signal processing circuitry.

10. The electronic device according to claim 7, wherein, the light sensing unit comprises:
   a first fingerprint sensor, configured to collect a first light signal for the fingerprint recognition and red light for health testing, and
   a second fingerprint sensor, configured to collect a second light signal for the fingerprint recognition and green light for health testing;

the signal processing unit comprises:
   a first fingerprint signal processing circuitry, connected to the control unit and configured to obtain a first fingerprint signal by processing the first light signal collected by the first fingerprint sensor;
   a red light signal processing circuitry, connected to the control unit and configured to obtain a red light signal by processing the red light collected by the first fingerprint sensor;
   a second fingerprint signal processing circuitry, connected to the control unit and configured to obtain a second fingerprint signal by processing the second light signal collected by the second fingerprint sensor; and
   a green light signal processing circuitry, connected to the control unit and configured to obtain a green light signal by processing the green light collected by the second fingerprint sensor;
the optical fingerprint module further comprises:
   a second circuit gating switch, in which one terminal of the second circuit gating switch is connected to the first fingerprint sensor, and the other terminal of the second circuit gating switch is connected to either the first fingerprint signal processing circuitry or the red light signal processing circuitry; and
   a third circuit gating switch, in which one terminal of the third circuit gating switch is connected to the second fingerprint sensor, and the other terminal of the third circuit gating switch is connected to either the second fingerprint signal processing circuitry or the green light signal processing circuitry;
the control unit is configured to:
   generate the fingerprint information for the fingerprint recognition based on at least one of the first fingerprint signal output by the first fingerprint signal processing circuitry and the second fingerprint signal output by the second fingerprint signal processing circuitry; and
   generate the health parameter information based on at least one of the red light signal output by the red light signal processing circuitry and the green light signal output by the green light signal processing circuitry.

11. The electronic device according to claim 9, wherein the optical fingerprint module further comprises at least one of:
   a red light emitting end, configured to emit the red light for the health testing; and
   a green light emitting end, configured to emit the green light for the health testing.

12. The electronic device according to claim 7, wherein the health parameter information comprises at least one of: value of heart rate, value of blood oxygen, and value of blood pressure.

13. A method for processing a signal, applicable to an electronic device comprising an optical fingerprint module, wherein the method comprises:
   determining a pre-defined health testing condition and a pre-defined fingerprint recognition condition;
   inputting a first light signal for health testing collected by a light sensing unit of the optical fingerprint module to a signal processing unit of the optical fingerprint module, and generating health parameter information based on a health signal output by the signal processing unit, in cases that the health testing condition is met; and
   inputting a second light signal for fingerprint recognition collected by the light sensing unit to the signal processing unit and generating fingerprint information for the fingerprint recognition based on a fingerprint signal output by the signal processing unit in cases that the fingerprint recognition condition is met;

wherein the optical fingerprint module comprises:

a light sensing unit, configured to collect a light signal;

a signal processing unit, connected to the light sensing unit and configured to generate at least one of a fingerprint signal and a health signal by processing the light signal collected by the light sensing unit; and a control unit, connected to the signal processing unit and configured to generate fingerprint information for fingerprint recognition based on the fingerprint signal output by the signal processing unit and generate health parameter information based on the health signal output by the signal processing unit;

wherein, the light sensing unit comprises a fingerprint sensor, in which the fingerprint sensor is configured to collect the light signal for the fingerprint recognition and further configured to collect at least one of red light and green light for health testing;

the signal processing unit comprises:

a fingerprint signal processing circuitry, connected to the control unit and configured to obtain the fingerprint signal by processing the light signal collected by the fingerprint sensor; and at least one of:

a red light signal processing circuitry, connected to the control unit and configured to obtain a red light signal by processing the red light collected by the fingerprint sensor; or a green light signal processing circuitry, connected to the control unit and configured to obtain a green light signal by processing the green light collected by the fingerprint sensor; and the optical fingerprint module further comprises:

a first circuit gating switch, configured to directly connect the fingerprint sensor to the fingerprint signal processing circuitry in response to the light signal collected by the fingerprint sensor is visual light signal, directly connect the fingerprint sensor to the red light signal processing circuitry in response to the light signal collected by the fingerprint sensor is red light signal, and directly connect the fingerprint sensor to the green light signal processing circuitry in response to the light signal collected by the fingerprint sensor is green light signal; and the control unit is configured to generate the fingerprint information for the fingerprint recognition based on the fingerprint signal output by the fingerprint signal processing circuitry, generate the health parameter information based on the red light signal output by the red light signal processing circuitry, or generate the health parameter information based on the green light signal output by the green light signal processing circuitry.

14. The method according to claim 13, further comprising:

determining whether a touch event is detected within a fingerprint recognition region formed on a touch and display module of the electronic device;

wherein meeting the fingerprint recognition condition comprises detecting that the touch event is within the fingerprint recognition region.

15. The method according to claim 14, wherein, meeting the fingerprint recognition condition further comprises determining that a pressing force corresponding to the touch event is not less than a preset pressure value, in response to detecting that the touch event is within the fingerprint recognition region.

16. The method according to claim 13, further comprising:

determining whether a preset function of the electronic device is in an on state;

wherein meeting the health testing condition comprises: the preset function being in the on state.

* * * * *